(12) United States Patent
Nilsson et al.

(10) Patent No.: US 11,738,136 B2
(45) Date of Patent: Aug. 29, 2023

(54) CONNECTOR SYSTEM FOR A NEGATIVE PRESSURE WOUND THERAPY SYSTEM

(71) Applicant: Mölnlycke Health Care AB, Gothenburg (SE)

(72) Inventors: Carianne Nilsson, Lerum (SE); Alain Roux, Träslövslage (SE)

(73) Assignee: Mölnlycke Health Care AB, Gothenburg (SE)

( * ) Notice: Subject to any disclaimer, the term of this patent is extended or adjusted under 35 U.S.C. 154(b) by 417 days.

(21) Appl. No.: 16/344,581

(22) PCT Filed: Oct. 24, 2017

(86) PCT No.: PCT/EP2017/077186
§ 371 (c)(1),
(2) Date: Apr. 24, 2019

(87) PCT Pub. No.: WO2018/086876
PCT Pub. Date: May 17, 2018

(65) Prior Publication Data
US 2020/0054804 A1   Feb. 20, 2020

(30) Foreign Application Priority Data
Nov. 10, 2016   (EP) .................... 16198139

(51) Int. Cl.
*A61M 1/00* (2006.01)
*A61M 39/10* (2006.01)

(52) U.S. Cl.
CPC ............. *A61M 1/86* (2021.05); *A61M 1/918* (2021.05); *A61M 1/94* (2021.05); *A61M 39/105* (2013.01);
(Continued)

(58) Field of Classification Search
CPC .......... A61M 1/86; A61M 1/85; A61M 1/964; A61M 39/105; A61M 1/90; A61M 39/00;
(Continued)

(56) References Cited

U.S. PATENT DOCUMENTS

2005/0004534 A1*  1/2005  Lockwood .............. A61M 1/74
                                                   604/304
2009/0030383 A1*  1/2009  Larsen .................. A61M 1/743
                                                   604/315

(Continued)

FOREIGN PATENT DOCUMENTS

WO   WO-2003/057070 A2   7/2003
WO   WO-2010/094957 A1   8/2010
WO   WO-2011/087871 A2   7/2011

OTHER PUBLICATIONS

International Search Report and Written Opinion dated Feb. 5, 2018 by the International Searching Authority for Patent Application No. PCT/EP2017/077186, which was filed on Oct. 24, 2017 and published as WO 2018/086876 on May 17, 2018 (Inventor—Nilsson et al.; Applicant—Mölnlycke Health Care AB) (13 pages).

*Primary Examiner* — Sarah Al Hashimi
*Assistant Examiner* — Nhu Q. Tran
(74) *Attorney, Agent, or Firm* — Ballard Spahr LLP

(57) ABSTRACT

The present disclosure relates to a connector device for a negative pressure wound therapy system having a connector housing, a fluid outlet connected to the connector housing, an air feeding port and an air filter and coupling means. The fluid outlet is adapted to be connected to a negative pressure source. The connector device is adapted to be engaged with a wound side connector of a wound side assembly by means of the coupling means. The wound side assembly includes a fluid removing conduit and an air supplying conduit, wherein a portion of each one of the fluid removing conduit and the air supplying conduit is connected to the wound side
(Continued)

connector. The connector device when engaged with the wound side connector, the fluid removing conduit is fluidly connected to the fluid outlet and the air supplying conduit is fluidly connected to the air feeding port such that air ambient of the connector device can be fed to the air supplying conduit via the air feeding port and the air filter.

13 Claims, 4 Drawing Sheets

(52) U.S. Cl.
CPC ..... *A61M 1/964* (2021.05); *A61M 2205/7536* (2013.01); *A61M 2205/8206* (2013.01)

(58) Field of Classification Search
CPC .......... A61M 39/10; A61M 2039/1033; A61M 2039/1077; A61M 2039/1083; A61M 2039/1088
See application file for complete search history.

(56) References Cited

U.S. PATENT DOCUMENTS

| | | | |
|---|---|---|---|
| 2012/0116334 A1* | 5/2012 | Albert | A61F 13/02 604/319 |
| 2012/0184931 A1 | 7/2012 | Horn | |
| 2013/0131616 A1* | 5/2013 | Locke | A61M 1/0023 604/321 |
| 2014/0330224 A1* | 11/2014 | Albert | A61F 13/0206 604/319 |
| 2016/0199551 A1* | 7/2016 | Bannister | A61M 39/0247 604/319 |

* cited by examiner

… … …

CONNECTOR SYSTEM FOR A NEGATIVE PRESSURE WOUND THERAPY SYSTEM

CROSS-REFERENCE TO RELATED APPLICATIONS

This application is a U.S. National Phase Application of International Application No. PCT/EP2017/077186, filed Oct. 24, 2017, which claims priority to European Application No. 16198139.4, filed Nov. 10, 2016, each of which are hereby incorporated by reference in their entirety.

TECHNICAL FIELD

The present disclosure relates to a connector device. More specifically, the present disclosure relates to a connector device for a negative pressure wound therapy system. Moreover, the present disclosure relates to a method of connecting the connector device to a wound side assembly.

BACKGROUND

Some types of wound are advantageously treated by so called negative pressure wound therapy. In the field of negative pressure wound therapy, a negative pressure is applied to the wound for a relatively long time and it has been realized that the healing process may be expedited by using such wound therapy.

To this end, a negative pressure wound therapy system may be used which generally comprises a wound cover member and an underlying wound filler that is adapted to be placed over a wound. The system further generally comprises a negative pressure source, such as a vacuum pump, which is in fluid communication with the wound site via a suction interface attached to the wound cover member and a fluid communication assembly comprising fluid conduit(s). The negative pressure source furthermore generally comprises a canister for collection of wound exudate removed from the wound site via the fluid communication assembly.

For convenient assembly of the negative pressure source with a fluid communication assembly, the negative pressure source may as well be provided with fluid conduit(s) comprising coupling means in the end portion, e.g. an end portion distal to the portion connected to the negative pressure source, allowing coupling connection with an end portion of the fluid conduit(s) of the fluid communication assembly, e.g. an end portion distal to the portion of the fluid conduit(s) connected to the suction interface, via corresponding, such as mating, coupling means.

Negative pressure wound therapy systems may generally be divided into two categories, single conduit devices and multiple conduit devices. A single conduit device comprises a single suction conduit providing the suction interface and consequently the wound site with a negative pressure. This single conduit also removes and transports wound exudate from the wound site to a negative pressure source. The negative pressure is normally a pump and is also provided with a canister to collect exudate. The multiple conduit devices additionally comprise one conduit supplying gas, such as air, to the suction interface in order to provide flushing and removal of wound exudate from the suction conduit, this gas flow may be air circulated from the pump.

In negative pressure wound therapy systems, there is in principle always a static pressure difference introduced by gravity between the pressure inside the canister and the pressure at the wound site. This is due to the height difference between the negative pressure wound therapy device and the wound site and a liquid column of exudate often present in the suction conduits. A problem relating to a change in the static pressure, decrease or increase, is due to the liquid column phenomena and may affect the ability to provide the correct level of negative pressure at the wound site when compared to the pressure at the negative pressure source canister. This issue may have undesired consequences on the pressure at the wound site. One possible consequence is pooling of exudate, which in turn can cause leakage due to detachment of the wound cover and even maceration of surrounding skin.

There is also a need for quick disconnection of the conduits with the dressing and suction interface still in place, for instance when the patient should take a shower, or undergo certain examinations, such as an MRI or X ray. Furthermore, there is still a need to avoid imprints that could be caused by non-soft components in the sensitive skin close to wound site.

SUMMARY

One object of the present disclosure is to provide a connector device for a negative pressure wound treatment system allowing the provision of a correct level of negative pressure at the wound site with a flexible, safe and convenient system.

This and other objects of the present disclosure may be achieved by a connector device according to the appended claims.

As such, the present disclosure relates to a connector device for a negative pressure wound therapy system. The connector device comprises a connector housing, a fluid outlet connected to the connector housing, an air feeding port, an air filter and coupling means. The fluid outlet is adapted to be connected to a negative pressure source. The connector device is adapted to be engaged with a wound side connector of a wound side assembly by means of the coupling means. The wound side assembly comprises a fluid removing conduit and an air supplying conduit, wherein a portion of each one of the fluid removing conduit and the air supplying conduit is connected to the wound side connector. The connector device is such that when the connector device is engaged with the wound side connector, the fluid removing conduit is fluidly connected to the fluid outlet and the air supplying conduit is fluidly connected to the air feeding port such that air ambient of the connector device can be fed to the air supplying conduit via the air feeding port and the air filter.

By filter herein is meant a material, such as a porous material, through which air may pass but which captures elements, such as particles, bacteria and spores from the ambient air. The filter may be a three-dimensional porous material component, such as, a cylindrical, rectangular or square shaped porous material component. For example, the porous material may be a sintered plastic, wherein the air flow through a sintered plastic material may be controlled by adapting the pore size (porosity) thereof.

The connector housing is provided with an air feeding port to there through allow ambient air to enter the air supplying conduit of the wound side assembly when coupled to the connector device and thereby provide a flushing functionality to the fluid removing conduit.

The fact that the connector device allows air to be fed via the air filter and the air feeding port ensures that ambient air enters the connector housing in a controlled and continuous manner and allows e.g. particles and potentially harmful bacteria to be captured.

The wound side assembly may be connectable to a suction interface being attached or being attachable to a wound cover material. The fluid removing conduit is adapted to remove fluid from a wound, through an opening provided in the wound cover material and through the suction interface attached to the wound cover material. The air supplying conduit is adapted to supply air through at least a portion of the suction interface and into the fluid removing conduit to provide flushing of the fluid removing conduit.

The connector device is thus intended to be attached at a distance from a wound site, with the wound side assembly as an intermediate module. This has found to be advantageous in that assemble or disassemble of the modules, i.e. the wound side assembly and the connector device, are effected at a distance from the wound site, which is more convenient for both the patient and the person performing assemble and/or disassemble of the connector device. Additionally, the risk of imprints from the connector on the patient's skin is reduced. To perform the assemble or disassemble of the modules at a distance from the suction interface is also safer in terms of decreased risk of infection and a reduced risk to in other ways harm to the wound.

Optionally, the connector device comprises an air feeding conduit comprising the air feeding port and an air inlet opening. The air feeding conduit is an integrated part of the connector housing.

Optionally, the air filter is completely integrated within air feeding conduit and the connector housing.

Optionally, the air filter is provided within an air filter housing provided with at least one air inlet opening allowing air to flow through the air filter. Optionally, the air filter housing is provided with at least two or at least three air inlet openings to ensure sufficient air flow.

The air filter housing may either be provided as an integrated part of the connector housing or as a separate compartment.

The fact that the air feeding conduit is an integrated part of the connector housing or that the air filter is provided within an air filter housing is specifically an advantage for a connector device according to the present disclosure due to the modularity of the system and that the connector device is an intermediate module intended to be positioned at a distance between the patient and the negative pressure source and thus exposed to the surroundings. For example, in embodiments of the present disclosure, the connector device is positioned at a distance of at least 5 cm, such as 10 cm, from the wound side connector. For example, the connector device may be positioned at a distance of between 5 to 20 cm from the wound side connector. In embodiments of the present disclosure, the connector device is positioned at a relatively equal distance between the patient and the negative pressure source, which may typically be about 60 to 80 cm from the wound side connector. The risk of a separate part or a non-protected air filter getting caught somewhere or being obstructed has been found particularly important for this type of connector device.

The air filter situated in a connector at a distance from the wound site cause less risk of obstruction, such as by wound cover films or adhesive tapes or similar unintentionally applied on top of it for fixation or underneath it for padding to avoid imprints.

Optionally, the connector housing has a connector housing device side and a connector housing coupling side, where the connector device is adapted to be connected to the wound side assembly at the connector housing coupling side. The air inlet opening is provided on the connector housing device side.

Optionally, the fluid outlet is also provided on the connector housing device side.

Optionally, the connector housing device side is positioned on the opposite side of the connector housing coupling side.

The connector device may be provided as a separate part interconnecting the wound side assembly and the negative pressure source via a conduit extending from the negative pressure source. The connector device may also be provided at the end of a fluid conduit(s) extending from, or adapted to connect to, the negative pressure source.

When the connector device is supplied as a separate part, i.e. without any conduits connected thereto, it may be provided device side coupling means at the connector housing device side for connection of the connector device with a negative source side assembly comprising a fluid removing conduit being connected to a negative pressure source side connector.

The fact that the air inlet opening is provided on the connector housing device side implies that the air inlet opening is provided on a side of the connector housing, and thus not on a part of the connector housing facing upwards or downwards when placed on a surface, such as a bed, during use, which reduces the risk for obstruction of the air inlet opening. An advantage coherent with air inlet opening being provided at the same side as the fluid outlet is that the proximity to a protruding part further minimizes the risk for obstructing the air inlet opening.

Optionally, the connector housing device side may be positioned on the opposite side of the connector housing coupling side.

Optionally, the air inlet opening is arranged at a radial distance from the fluid outlet.

The fact that the connector housing device side, and thus the air inlet opening, is provided on the opposite side of the connector housing coupling side additionally to the advantages described above, ensures a straight fluid and air passage, minimizing the risk for obstruction of the air inlet opening. That the air inlet opening is arranged at a radial distance from the fluid outlet also minimizes the risk of obstruction of the air inlet opening and possible protruding parts at the connector device.

Optionally, the air filter is at least partly located within said connector housing so that maximum 2 cm of the air filter protrudes outside the connector housing, or maximum 1 cm of the air filter protrudes outside the connector housing, or maximum 0.5 cm of the air filter protrudes outside the connector housing.

Optionally, a fluid conduit is connected to the fluid outlet. Optionally, a portion of the fluid conduit, being a portion opposite to the side connected to the connector device, is connected to a device side connector comprising coupling means adapted to be connected to a negative pressure source side connector.

Optionally, the air filter provides an air leakage of between 0.5 to 70 ml/min at a pressure of 120 mmHg, or between 1 to 40 ml/min at a pressure of 120 mmHg.

Optionally, the air filter provides an air leakage of between 10 ml/min to 70 ml/min at a pressure of 120 mmHg, or between 15 ml/min to 55 ml/min at a pressure of 120 mmHg.

At high air leakage rates, the pump has to work harder, which in turn can have negative effects on noise and battery consumption. It is also more difficult to maintain a controlled therapy pressure at the wound site. At lower air leakage rates, efficient exudate removal is difficult to obtain. It is therefore important to find a good balance between those different parameters.

In embodiments of the present disclosure, the air filter may advantageously be adapted to provide an air leakage of about 1 to 5 ml/min, for example about 1.5 to 2.5 ml/min, such as about 2 ml/min, thereby reducing noise and battery. An air leakage rate in the range of about 1 to 5 ml/min may in particular be advantageous in case a relatively small pump is being used, e.g. a pump with a suction capacity of up to around 1.0 liter/min (e.g. suction capacity between 0.1 to 1.0 liter/min, such as 0.5 liter/min) and with relatively limited battery capacity.

In embodiments of the present disclosure, in particular when a pump with a suction capacity of more than 1.0 liter/min being used, e.g. a suction capacity of from 1.5 to 5 liter/min, the air filter may be adapted to provide an air leakage of 10 to 30 ml/min, for example 15 to 25 ml/min, such about 20 ml/min.

The continuous and controlled inflow of air allows the creation of an air flow well defined at all values of relevant negative pressure minimizing the problems of liquid column phenomena. The connector device according to the present disclosure thus provides an improved and secure negative pressure wound therapy which is simple to handle and requires less supervision.

Optionally, the connector device coupling means are adapted to form a snap-on, threaded, luer-lock or bayonet engagement with the wound side connector.

Optionally, the connector device coupling means are adapted to form a release snap-on, threaded or bayonet engagement with the wound side connector.

A second aspect of the present disclosure relates to a branched connector device. The branched connector device comprises a branched conduit which in turn comprises a first and at least a second branch portion. The branched connector device further comprises a connector device according the first aspect of the present disclosure, wherein the first branch portion is connected to the fluid outlet of the connector device.

Optionally, a portion of the second branch portion, being a portion opposite to the side of the conduit connected to the connector device, is connected to a device side connector comprising coupling means adapted to be connected to a negative pressure source side connector.

Optionally, the branched connector device comprises a second connector device comprising a second connector housing and coupling means and a second fluid outlet connected to the second connector housing and wherein the second branch portion is connected to the second fluid outlet.

The fact that the branched connector device comprises a second connector device comprising coupling means allows for easy connection to more than one fluid communication assembly, while providing air supply and flushing functionality to the fluid removing conduit(s).

The second connector device may, for example, by means of second coupling means be connected to a second wound side assembly comprising a fluid removing conduit adapted to connect to a suction interface and to remove fluid therethrough.

Such a branched connector device allows for simple treatment of larger wounds or multiple wounds.

Optionally, the second connector device comprises a second air feeding port.

Such a branched connector device allows connection of one single negative pressure source to at least two wound sites via two wound fluid communication assemblies, each comprising a fluid removing conduit and an air supplying conduit, and each being able to connect to a suction interface, ensuring the provision of a correct level of negative pressure at each of the wound sites.

The capacity of the branched connector device to maintain the correct level of negative pressure at each of the wound sites while only needing one single negative pressure source and without constantly needing to adjust the negative pressure from each of the negative pressure sources to ensure correct levels at the wound size leads to an improved and secure wound treatment which is simple to handle and requires less supervision.

Optionally, a second conduit is connected to the second air feeding port.

Optionally, the second conduit and the branched conduit are provided with coupling means at the end portions for coupling connection with, for example, a further connector device provided with a fluid outlet and an air feeding port comprising an air filter, such as a connector device according to the first aspect of the present disclosure. This provides a fluid passage to the negative pressure source while ensuring an ambient air supply to the second air feeding port even though connected to a second conduit.

Optionally, the second connector device is a connector device according the first aspect of the present disclosure.

Optionally, the branched connector device is a Y-connector device.

Optionally, the branched conduit comprises a third branch portion which is connected to a third fluid outlet of a third connector device.

A third aspect of the disclosure relates to a method comprising providing a connector device according to the first aspect of the present disclosure, connecting the connector device to a wound side assembly comprising a fluid removing conduit and an air supplying conduit, by further connecting said fluid removing conduit to said first fluid outlet and said air supplying conduit to said air feeding port via said connector housing.

Optionally, the method further comprises applying negative pressure to a suction interface via the fluid outlet and the fluid removing conduit.

BRIEF DESCRIPTION OF THE DRAWINGS

The various aspects of the present disclosure, including its particular features and advantages will be readily understood from the following detailed description and the accompanying drawings, in which:

FIG. 2a illustrates a perspective view of an embodiment of a connector device;

FIG. 2b illustrates a cross sectional view of the connector device according to FIG. 2a;

DETAILED DESCRIPTION

Figure 1:
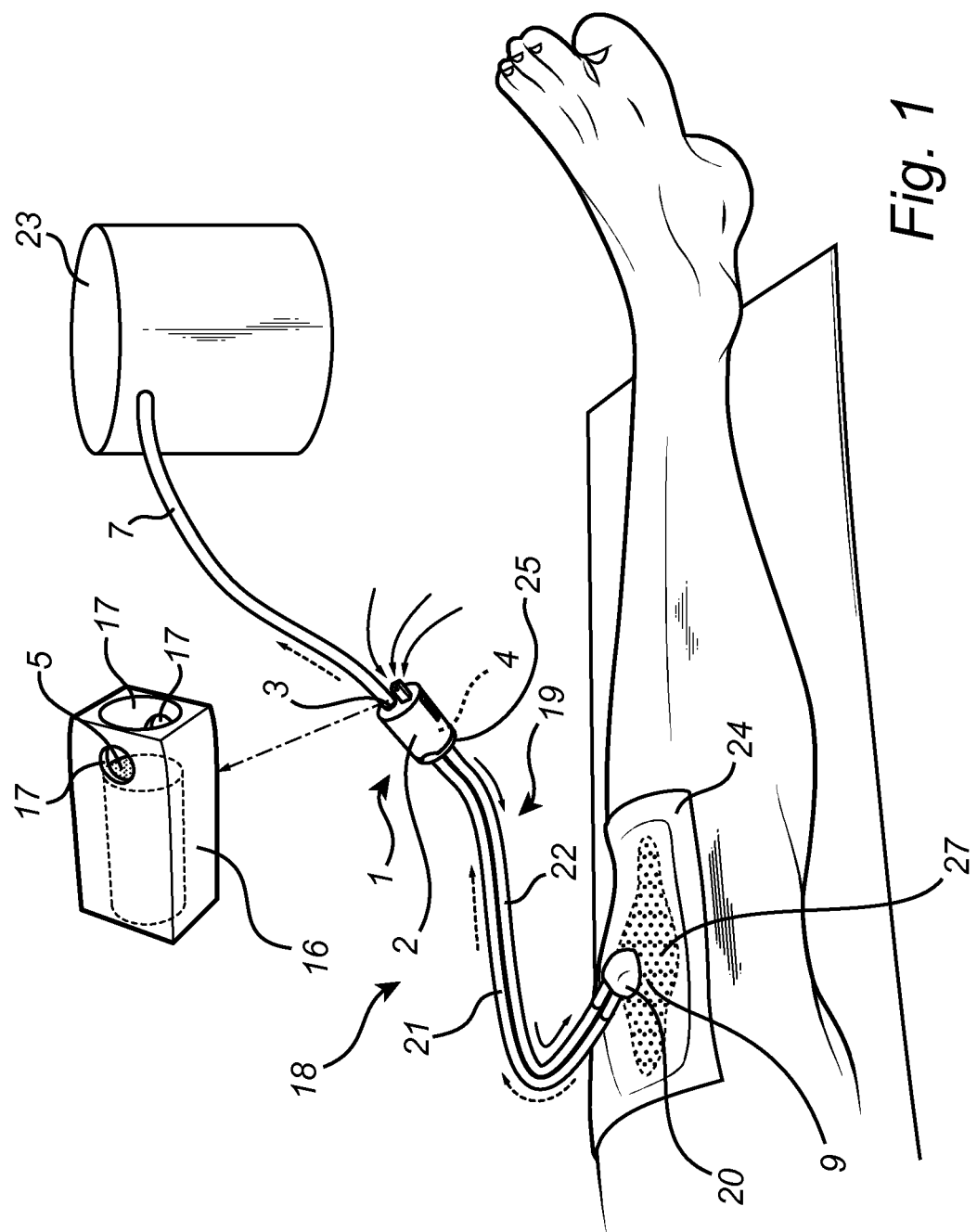
FIG. 1 illustrates an embodiment of a negative pressure wound therapy system.

FIG. 1 illustrates a negative pressure wound therapy system 18. The purpose of a negative pressure wound therapy system 18 is to obtain a negative pressure in the area of a wound 9.

The negative pressure wound therapy system illustrated in FIG. 1 comprises a negative pressure source 23, which in FIG. 1 is in the form of a vacuum pump. The negative pressure wound therapy system 18 according to FIG. 1 includes a wound cover member 24, attached over and covering the wound 9 and a wound filler 27, such as a foam or a gauze, placed on or in the wound to be treated by the negative pressure wound therapy system.

The wound cover member 24 is generally adapted to be attached to the skin surrounding the wound. Purely by way of example, the wound cover member 24 may comprise a wound cover film. The wound cover member 24 may preferably be attached to the skin by an adhesive. Examples of adhesives that may be used include, but are not limited to, acrylic adhesives and/or silicone gel adhesives.

Moreover, the negative pressure wound therapy system illustrated in FIG. 1 includes a suction interface 20 and a wound side assembly 19 comprising a fluid removing conduit 21 adapted to remove fluid, such as air and wound exudates, through the suction interface 20 and to a canister comprised in the negative pressure source 23 and an air supplying conduit 22 adapted to supply air through at least a portion of said suction interface 20 and directly in to the fluid removing conduit 21.

FIG. 1 further illustrates that the negative pressure wound therapy system 18 comprises a connector device 1 comprising a connector housing 2 and a fluid outlet 3 connected to the connector housing 2. The fluid outlet 3 is in FIG. 1 connected to a fluid conduit 7 connected to the negative pressure source 23 e.g. comprising a canister for collection of the wound exudate. The direction of the fluid in the negative pressure wound therapy system 18 is illustrated in FIG. 1 with the dotted arrows. The connector housing 2 further comprises an air feeding port 4 and an air filter 5 to create a controlled air leak to the suction interface 20. The direction of the air flow in the negative pressure wound therapy system 18 is illustrated in FIG. 1 with unbroken arrows. The air filter 5 may be a porous material filtering and capturing particles while allowing air to flow/leak through the porous structure. The air filter 5 may for example be a cylindrical, square or rectangular shaped porous material. The air leakage provided by the air filter 5 may be between 10 ml/min to 70 ml/min at a pressure of 120 mmHg, or between 15 ml/min to 55 ml/min at a pressure of 120 mmHg.

In embodiments of the present disclosure, the air leakage provided by the air filter 5 may be between 0.5 ml/min to 70 ml/min at a pressure of 120 mmHg, or between 1 ml/min to 40 ml/min at a pressure of 120 mmHg. For example, the air leakage provided by the air filter 5 may be between about 1 to 5 ml/min. For example, the air leakage provided by the air filter 5 may be between about 15 to 25 ml/min.

In FIG. 1 the air filter 5 is provided in an air filter housing 16, provided with at least one air inlet opening 17, and herein illustrated with three openings, being an integrated extending part of the connector housing 2. However, the air filter housing 16 may also be provided as a separate part, for example connected either directly to the connector housing 2.

The connector housing 2 comprises coupling means 6 for fluidly connecting the fluid removing conduit 21 to the fluid outlet 3 and the air supplying conduit 22 to the air feeding port 4 via the wound side connector 25.

In negative pressure wound therapy systems there is in principle always a static pressure difference introduced by gravity between the pressure inside the canister and the pressure at the wound site. This is due to the height difference between the negative pressure source 23 and the wound 9. The amount of exudate inside the fluid removing conduit 21 and the fluid conduit 7 may increase, decrease or not influence the pressure at the wound site compared with the pressure inside the canister depending on the orientation of the tubing. A purpose of introducing the air volume is to ensure that transport of exudates takes place, e.g. by preventing clogging in or moving exudate from the fluid removing conduit 21 and the fluid conduit 7, between the wound area and a canister provided in connection with the vacuum pump despite static pressure differences introduced by gravity and consequently secure a correct pressure level at the wound site.

Figure 2:
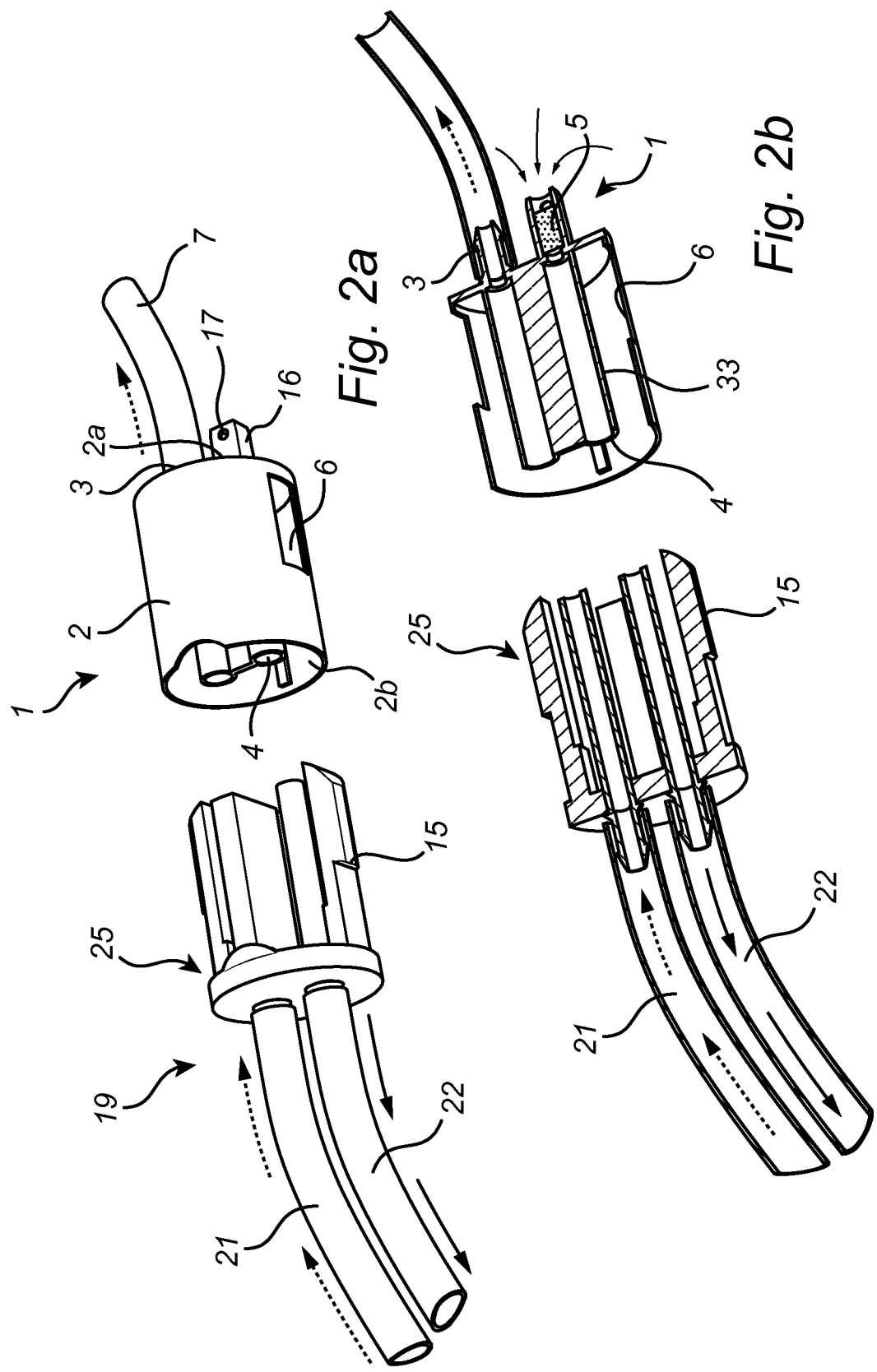

FIGS. 2a and 2b illustrate an embodiment of the connector device 1 according to the present disclosure, wherein FIG. 2b is a cross sectional view of the connector device according to FIG. 2a. The connector device 1 comprises a fluid outlet 3, connected to a fluid conduit 7 connectable to the negative pressure source 23. The fluid outlet may be in the form of an extending body portion provided with coupling means, such as gripping means for receiving and retaining fluid conduit 7, for fluid connection to the negative pressure source 23. The fluid conduit 7 may be, at a portion opposite to the side connected to the connector device, connected to a device side connector comprising coupling means adapted to be connected to a negative pressure source side connector. The wound side assembly 19 is provided with wound side assembly coupling means 15 for coupling connection with the connector device coupling means 6. Non-limiting example of a coupling connection is a snap-on, threaded, luer-lock and bayonet connections.

As clearly illustrated in FIG. 2b showing a cross sectional view of the connector device 1, the connector device 1 may comprise an air feeding conduit 33 comprising the air feeding port 4 and an air inlet opening 17. Moreover, as is indicated in FIG. 2b, the air feeding conduit 33 is an integrated part of the connector housing 2 and may accommodate the air filter 5 or may be connected to an air filter housing 16. The air feeding conduit 33 may be adapted to be connected to the air supplying conduit 22 and the fluid outlet 3 may be securely connected to the fluid removing conduit 21.

Figure 3:
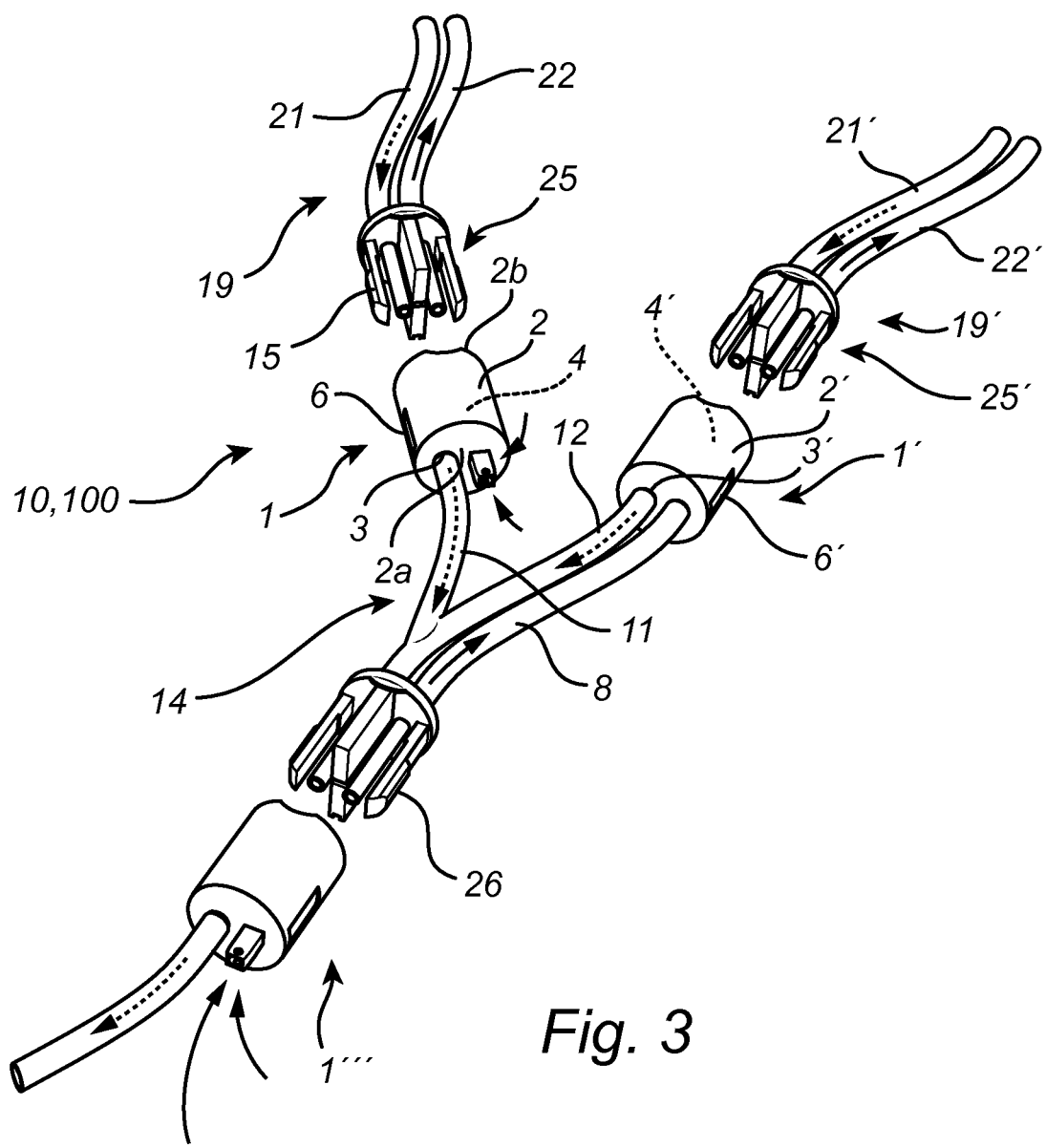
FIG. 3 illustrates a perspective view of an embodiment of a Y connector device and exemplified connecting parts.

FIG. 3 illustrates a branched connector device 10, and more specifically a Y connector device 100, according to the present disclosure. The Y connector device 100 illustrated in FIG. 3 comprises a first connector device 1 comprising a connector housing 2 and a fluid outlet 3 connected to the connector housing 2. The Y connector device 100 furthermore comprises a branched conduit 14 comprising a first and a second branch portion 11, 12, the fluid outlet 3 being directly connected to the first branch portion 11.

The direction of the fluid in the Y connector device 100 and the fluid communication assemblies is illustrated in FIG. 3 with the dotted arrows. The connector housing 2 further comprises an air feeding port 4 and an air filter 5 to create a controlled air leak via the air supplying conduit 22. The direction of the air in the Y connector device 100 and the fluid communication assemblies is illustrated in FIG. 3 with the unbroken arrows. The air filter 5 may be a porous material filtering and capturing particles while allowing air to flow/leak through the porous structure. The air filter 5 may be a three-dimensional porous material. The air leakage provided by the air filter 5 may be between 0.5 ml/min to 70 ml/min at a pressure of 120 mmHg. For example, the air leakage provided by the air filter 5 may be between 10 ml/min to 70 ml/min at a pressure of 120 mmHg, or between 15 ml/min to 55 ml/min at a pressure of 120 mmHg, or between 1 ml/min to 40 ml/min at a pressure of 120 mmHg, or between about 1 ml/min to 5 ml/min, or between about 15 to 25 ml/min.

Preferably, the air leakage provided by the air filter 5 is adapted such that a continuous flow of air is ensured via the air supplying conduit 22, whilst at the same time reducing unnecessary work load of the negative pressure source 23, thereby minimizing noise and battery usage from the negative pressure source 23. For example, in case the negative pressure source 23 has a suction capacity of up to about 1 L/min, the air leakage provided by the air filter 5 may preferably be adapted to be between about 1 to 5 ml/min at a pressure of 120 mmHg. For example, in case the negative pressure source 23 has a suction capacity of up to about 5 L/min, the air leakage provided by the air filter 5 may preferably be adapted to be between about 15 to 55 ml/min at a pressure of 120 mmHg, such as between about 15 ml/min to 25 ml/min at a pressure of 120 mmHg.

In FIG. 3 the air filter 5 is provided in an air filter housing 16, provided with three openings 17, being an integrated extending part of the connector housing 2. However, the air filter housing 16 may also be provided as a separate part, for example connected either directly to the connector housing 2.

The connector housing 2 comprises coupling means 6 for fluidly connecting the fluid removing conduit 21 to the fluid outlet 3 and the air supplying conduit 22 to the air feeding port 4. In FIG. 3 the connector device 1 is adapted to be connected to the wound side assembly 21 at the connector housing coupling side 2*b* and the air feeding port is provided on the connector housing device side 2*a*, which is positioned on the opposite side of the connector housing coupling side 2*b*.

In negative pressure wound therapy systems there is in principle always a static pressure difference introduced by gravity between the pressure inside the canister and the pressure at the wound. This is due to the height difference between the negative pressure wound therapy system 18' and the different wounds 9 and the fact that exudate often is present in the conduits. The liquid column of exudate inside the fluid removing conduit 21 and the fluid conduit 7 may increase, decrease or not influence the pressure at the wound site compared with the pressure inside the canister depending on the orientation of the tubing. A purpose of introducing the air volume is to ensure that transport of exudate takes place between the wound area and a canister provided in connection with the vacuum pump, despite static pressure differences introduced by gravity, and consequently secures a correct pressure at the wound site. This is an even more crucial issue for negative wound therapy systems connectable to more than one fluid communication assembly and thus able to perform treatment at more than one wound site using only one negative pressure source.

The wound side assembly 19 is provided with wound side assembly coupling means 15 for coupling connection with the connector device coupling means 6. A non-limiting example of a coupling connection is a snap-on connection.

The Y connector device 100 according to FIG. 3 furthermore comprises a second connector device 1', with a second connector housing 2' and a second fluid outlet 3', wherein the second branch portion 12 is connected to the second fluid outlet 3'. The second connector device 1' furthermore comprises a second air feeding port 4' connected to the second connector housing 2'. In FIG. 3, a second conduit 8 is connected to the second air feeding port 4'. However, it is also conceivable that the configuration of the air feeding port of the second connector device 1' is identical to the air feeding port configuration of the first connector device 1, shown in FIG. 1-2.

The second connector housing 2' furthermore comprises second coupling means 6' for fluidly connecting a second fluid removing conduit 21' to the second fluid outlet 3' and the second air supplying conduit 22' to the second air feeding port 4'. The second connector device 1' is adapted to be engaged with a second wound side connector 25' of a second wound side assembly 19' at the second connector housing coupling side 2*b*' or alternatively to a branched connector device 10, such as an Y connector device 100, according to the present disclosure.

The end portion of the branched conduit 14 is provided with a device side connector comprising coupling means 26 for coupling connection to a connector device 1'''. The connector device 1''' may be a connector device identical to the connector device 1, a branched connector device 10, such as a Y connector device 100, all comprising a fluid outlet for fluid communication with the first and second branch portions 11, 12 via the end portion of the branched conduit 14, and an air feeding port to supply air via the second conduit 8 to the air feeding port 3' of the second connector device 2'. It is of course also conceivable that the device side connector comprising coupling means 26 is coupled to a negative pressure source side connector connected to an fluid removing conduit leading to a negative pressure source 23 comprising a canister for receiving wound exudate.

Figure 4:
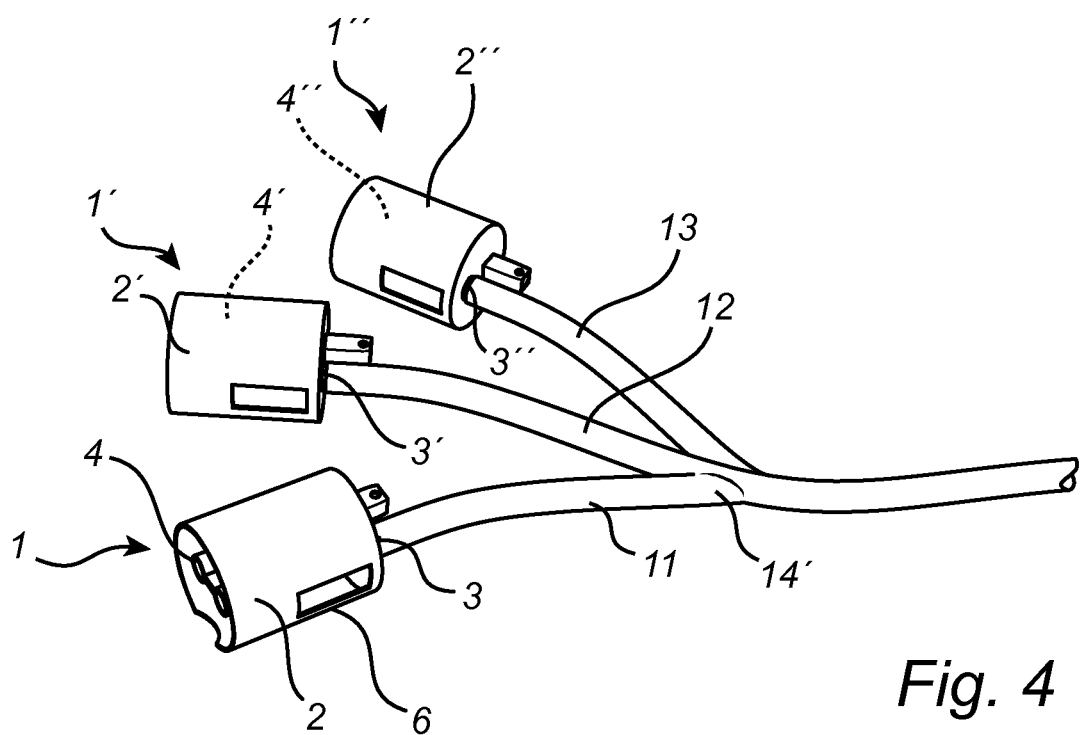
FIG. 4 illustrates a perspective view of an embodiment of a branched connector device.

FIG. 4 illustrates a further branched connector device 10. The branched connector device 10 illustrated in FIG. 4 comprises a first connector device 1 comprising a connector housing 2 comprising coupling means 6 and a fluid outlet 3 connected to the connector housing 2. The branched connector device 10 furthermore comprises a branched conduit 14' comprising a first, a second and a third branch portion 11, 12, 13, wherein the fluid outlet 3 is directly connected to the first branch portion 11.

The branched connector device 10 furthermore comprises a second connector device 1', with a second connector housing 2' and a second fluid outlet 3', wherein the second branch portion 12 is connected to the second fluid outlet 3'. The second connector device 1' furthermore comprises a second air feeding port 4' connected to the second connector housing 2'. A third connector device 1", with a third connector housing 2" and a third fluid outlet 3", is connected to the third branch portion 13 via the third fluid outlet 3". The third connector device 1" furthermore comprises a third air feeding port 4" connected to the third connector housing 2".

Each of the first, second and third connector devices 1, 1', 1" furthermore comprises air filters 5, 5', 5" provided in air filter housings 16, 16', 16".

As illustrated in FIG. 3 and FIG. 4, a unique advantage with the branched connector devices according to the present disclosure is that air is allowed to enter into each of the fluid communications assemblies connected via each of the connector devices ensuring flushing of each fluid communication assembly even when only one negative pressure source is used.

The invention claimed is:

1. A connector device for a negative pressure wound therapy system, said connector device comprising:
   a connector housing,
   a fluid outlet connected to said connector housing,
   an air feeding conduit comprising an air feeding port and an air inlet opening, said air feeding conduit being an integrated part of said connector housing, an air filter positioned within the air feeding conduit; and coupling means, wherein:
said fluid outlet is adapted to be connected to a negative pressure source, said connector housing has a connector housing device side and an opposing connector housing coupling side, wherein said fluid outlet and air inlet opening are provided on said connector housing device side, wherein said air inlet opening is arranged at a radial distance from said fluid outlet, said opposing connector housing coupling side of said connector device being adapted to be engaged with a wound side connector of a wound side assembly by means of said coupling means so that, when the opposing connector housing coupling side is engaged with the wound side connector of the wound side assembly, at least a portion of the wound side connector of the wound side assembly extends past the opposing connector housing coupling side of the connector housing in a direction toward the connector housing device side of the connector housing, said wound side assembly comprising a fluid removing conduit and an air supplying conduit, a portion of each one of said fluid removing conduit and said air supplying conduit being connected to said wound side connector, said connector device being such that when said connector device is engaged with said wound side connector, said fluid removing conduit is fluidly connected to said fluid outlet and, said air supplying conduit is fluidly connected to said air feeding port such that air ambient of said connector device can be fed to said air supplying conduit via said air filter and said air feeding port.

2. The connector device according to claim 1, wherein said air filter is provided within an air filter housing provided with said air inlet opening allowing air to flow through said air filter.

3. The connector device according to claim 1, wherein said air filter is at least partly located within said connector housing so that maximum 2 cm of said air filter protrudes outside said connector housing.

4. The connector device according to claim 1, wherein a fluid conduit is connected to said fluid outlet.

5. The connector device according to claim 1, wherein said air filter provides an air leakage of between 0.5 ml/min to 70 ml/min at a pressure of 120 mmHg.

6. The connector device according to claim 1, wherein said connector device by means of said coupling means is adapted to form a snap-on, threaded, luer-lock, or bayonet engagement, with said wound side connector.

7. A branched connector device comprising a branched conduit which in turn comprises a first and a second branch portion, said branched connector device further comprising the connector device according to claim 1, wherein said first branch portion is connected to said fluid outlet of said connector device.

8. The branched connector device according to claim 7, wherein said branched connector device comprises a second connector device comprising a second connector housing and second coupling means and a second fluid outlet connected to said second connector housing, said second branch portion being connected to said second fluid outlet.

9. The branched connector device according to claim 8, wherein said second connector device comprises a second air feeding port.

10. The branched connector device according to claim 9, wherein a second conduit is connected to said second air feeding port.

11. A method comprising providing the connector device according to claim 1, connecting the connector device by means of said coupling means with the wound side connector of the wound side assembly, said wound fluid side assembly comprising the fluid removing conduit and the air supplying conduit, a portion of each one of said fluid removing conduit and said air supplying conduit being connected to said wound side connector.

12. The method according to claim 11, further comprising applying suction to a suction interface via said fluid outlet and said flexible fluid removing conduit.

13. The connector device of claim 2, wherein the air filter housing and the fluid outlet extend parallel to each other.

\* \* \* \* \*